United States Patent [19]

Woiszwillo

[11] Patent Number: 5,006,461
[45] Date of Patent: Apr. 9, 1991

[54] TMB FORMULATION FOR SOLUBLE AND PRECIPITABLE HRP-ELISA

[75] Inventor: James E. Woiszwillo, Milford, Mass.

[73] Assignee: Transgenic Sciences, Inc., Worcester, Mass.

[21] Appl. No.: 431,485

[22] Filed: Nov. 3, 1989

[51] Int. Cl.[5] ................ C12G 1/00; G01N 33/53; C12Q 1/68; C12Q 1/28
[52] U.S. Cl. ........................ 435/7.92; 534/808; 435/6; 435/28; 435/863; 435/967
[58] Field of Search .............. 435/7, 6, 28, 803; 534/808

[56] References Cited

U.S. PATENT DOCUMENTS 4,789,630 12/1988 Bloch et al. .................... 435/28

OTHER PUBLICATIONS

Sax, N. I., et al., Hawley's Condensed Chemical Dictionary Van Nostrand Reinhold Co., Inc. 1987, pp. 34, 227, 1224, 1225, 725.

*Primary Examiner*—Robert A. Wax
*Assistant Examiner*—Bradley L. Sisson
*Attorney, Agent, or Firm*—Kilpatrick & Cody

[57] ABSTRACT

Solvent systems for use in increasing the solubility of 3,3',5,5'-tetramethylbenzidine (TMB) and for making a permanent color record of the results of ELISAs using HRP have been developed. In the improved solvent system containing povidone, 1-ethenyl-2-pyrrolidinone polymers, TMB can be dissolved in a very small quantity of solvent, up to a concentration of 100 to 200 mM, which can then be mixed directly into an aqueous buffer without precipitating the TMB. In the solvent system for making a permanent record, alginic acid (AA), methyl vinyl ether/maleic anhydride copolymer (MVE/MAC), dextran sulfate (DS) and/or carrageenan are added to the aqueous buffer solution, with or without povidone, to form a colored precipitate with the reaction product.

15 Claims, No Drawings

TMB FORMULATION FOR SOLUBLE AND PRECIPITABLE HRP-ELISA

This is generally in the area of ELISAs, and in particular relates to improved chromogenic solutions.

The Enzyme-Linked ImmunoSorbant Assay, or ELISA, is a well accepted and widely utilized method used in both qualitative and quantitative assays for biomolecules. In one embodiment of this assay, an enzyme is linked to an antibody to the molecule to be measured, and then used in combination with a chromogenic substrate for that enzyme which yields a colored reaction product. The molecule to be measured is immobilized on a solid phase such as a test tube or filter membrane. For example, as described in *J. Immunoassay* 2(3 and 4), 187–204 (1981), HorseRadish peroxidase (HRP) is chemically coupled to an antibody and the conjugate incubated with a solution containing a chromogenic substrate such as urea peroxide, a chromogen that changes color when urea peroxide is oxidized, and an appropriate buffer such as 0.03 M citrate-acetate or 0.1 M citrate-phosphate, pH 5.0. The formation of colored product can be qualitatively observed or quantitatively measured by absorption spectrophotometry. The rate and extent of color formation is proportional to the concentration of antigen. There are numerous other variations of this assay, using different enzymes and chromogenic substrates.

The most sensitive chromogen as of this time for use with HRP is 3,3',5,5'-tetramethylbenzidine (TMB), as first reported by E. S. Bos, et al., in *J. Immunoassay* 2(3 and 4), 187–204 (1981). Unlike other benzidine compounds, this derivative is not mutagenic as determined using the Ames test. TMB, which is relatively insoluble in aqueous solutions, works best when first dissolved in a water-miscible solvent such as dioxane, dimethylformamide (DMF), or dimethylsulfoxide (DMSO), rather than in solvents such as the lower alcohols, diethylether and aromatic solvents. For example, as described by Bos, et al., (1981), TMB is dissolved in DMSO up to 42 mM, and diluted into 0.1 M sodium acetate-citric acid buffer, pH 6.0. This is mixed with 1.3 mmole hydrogen peroxide or 0.5 mmole urea hydrogen peroxide immediately before addition of the conjugate, which reacts to turn the solution blue. Addition of acid stops the reaction and converts the blue color to a yellow color that can be measured at 450 nm using a standard spectrophotometer. Both the untreated blue solution and the acidified yellow solution fade over time, leaving only the recorded absorbance as a permanent record.

It is important to reduce background signal by reducing non-specific binding of HRP conjugate to the plastic or membrane. This is generally accomplished by incubating the solid support with bovine serum albumin (BSA) or casein in either carbonate buffer, pH 9, or phosphate buffer, pH 7, prior to addition of the conjugate and substrate, as described in *Antibodies. A Laboratory Manual*, pp 182–183 (Cold Spring Harbor 1988). The TMB (0.1 ml of a 1 mg TMB/ml solution) is then added to the phosphate buffer (9.9 ml) and the extent of reaction measured. Generally, concentrations of less than 10 mM are added to the buffer containing the substrate.

The TMB reaction product does not precipitate out of solution and therefore cannot be used with commercial ELISA sampling devices to leave a "permanent" color record. However, some reagents which do produce a permanent record have been developed. For example, the chromogen 3,3'-diaminobenzide tetrahydrochloride (DAB), oxidizes to a reddish brown precipitate which is deposited at the site of the enzyme reaction. This may be used for immunoblotting and immunohistochemical staining. However, DAB is less sensitive than TMB, is unstable in solutions, fades over time, and is carcinogenic. Another example of a commercial assay system which produces a precipitate is the TMB containing system distributed by Kirkegaard & Perry Laboratories, Gaithersburg, Md., which contains a peroxidase substrate, and "an enhancer" that reacts with the peroxidase labeled antibodies to produce a blue precipitate on nitrocellulose membranes.

There remains a need for a sensitive, versatile chromogenic substrate system for use with HRP enzyme assays. In addition, there is a continued need to have a simple, stable method for producing a permanent color record of the assay results.

It is therefore an object of the present invention to provide a method and compositions for enhancing the utility of ELISA procedures using TMB as the chromogen.

It is another object of the present invention to provide a method and compositions for creating a permanent color record of the results in ELISA procedures using TMB as the chromogen.

SUMMARY OF THE INVENTION

Solvent systems for use in increasing the solubility of 3,3',5,5'-tetramethylbenzidine (TMB) and for making a permanent color record of the results of ELISAs using HRP have been developed.

In the improved solvent system containing povidone, 1-ethenyl-2-pyrrolidinone polymers, TMB can be dissolved in a very small quantity of solvent, up to a concentration of 100 to 200 mM, which can then be mixed directly into an aqueous buffer without precipitating the TMB. In the preferred embodiment, the TMB is preferably dissolved in an organic solvent containing between 1 and 10% povidone, to a concentration of between 10 and 100 mM, depending on the application. Advantages to this new solvent system for HRP ELISAs include a reduction in the amount of expensive, toxic organic solvents that is required.

In the solvent system for making a permanent record, alginic acid (AA), methyl vinyl ether/maleic anhydride copolymer (MVE/MAC), dextran sulfate (DS) and/or carrageenan are added to the aqueous buffer solution, with or without povidone, to form a colored precipitate with the reaction product. In the preferred embodiment, between 0.1 and 1.0 mg/ml of polymer are added to the buffer.

DETAILED DESCRIPTION OF THE INVENTION

Reagents are provided for use in ELISA procedures utilizing TMB as the chromogen in combination with peroxidase conjugates. In the preferred reagent, TMB is dissolved in a solvent such as DMF, methanol or DMSO, to a concentration of greater than 10 mM, preferably between 10 and 100 mM, most preferably between 20 and 40 mM, then added to an aqueous buffer, preferably citrate acetate or citrate phosphate containing an appropriate peroxidase substrate, such as 1 to 10 mM hydrogen peroxide or urea hydrogen peroxide, and from 1% to 10% by volume povidone, preferably 1 to 5%, to form an aqueous solution of between approximately 0.3 and 1.5 mM TMB. Povidone having a molecular weight of 24,000 and/or 40,000 is used to obtain a preferred viscosity. The reaction with the peroxidase conjugate is stopped by addition of acid, for example, 1 to 2 N sulfuric acid, which yields a spectrophotometrically measurable yellow color.

In contrast to the prior art methods in which TMB is dissolved in organic solvents to a maximum concentration of from 1 to 2 mM, and then mixed with aqueous buffers containing the HRP substrate and chromogen, the improved povidone solvent system allows the TMB to be dissolved up to a much greater concentration, thereby introducing a significantly smaller quantity of organic solvent into the aqueous buffer-substrate-reaction mixture.

If a colored precipitate is desired, alginic acid (AA), methyl vinyl ether/maleic anhydride copolymer (MVE/MAC), dextran sulfate (DS) and/or carrageenan (CA) are added to the aqueous buffer-TMB/povidone solution. These compounds form a colored precipitate indicative of the production of oxidation products of peroxidase.

The following concentration ranges of precipitating polymer can be used:

TABLE 1

Polymer Concentration Ranges for formation of Precipitate in ELISA with TMB

| Polymer | Concentration (mg/ml): | |
|---|---|---|
| | Useful Range | Preferred Range |
| alginic acid | 0.1–1.0 | 0.3–0.7 |
| methyl vinyl ether/ maleic anhydride copolymer | 0.1–2.0 | 0.5–1.5 |
| dextran sulfate | 0.1–2.0 | 0.3–0.6 |
| carrageenan | 0.3–1.0 | 0.6–1.0 |

These compounds can also be used with organic solutions not containing povidone and will yield precipitates in solutions having a pH range from at least 3.0 to 7.0.

As used herein, 3,3',5,5'-tetramethylbenzidine or derivatives thereof producing a color change upon exposure to oxidizing agents, such as 3,3',5,5'-tetramethylbenzidine dihydrochloride (described by Liem, et al., *Anal. Biochem.* 98, 88–393 (1979)), are referred to as TMB. When oxidized, the TMB forms a blue color with maximum absorption at 650 nm. The addition of acid stops the reaction and changes the color to yellow, with a maximum absorption at 450 nm. Other chromogens besides TMB which can be used with horseradish peroxidase include chloro/naphthol, diaminobenzidine tetrahydrochloride, aminoethylcarbizole, and ortho phenylenediamine.

Reagents for use in ELISA procedures, including HRP-antibody conjugates and TMB, are commercially available from a variety of sources, for example, Organon Teknika-Cappel, West Chester, Pa., and ICN ImmunoBiologicals, Lisle, Ill. As sold by Organon Teknika-Cappel, the TMB is provided as a 1.5% solution for dilution into 30 to 150 ml of working solution.

1-ethenyl-2-pyrrolidone polymers, referred to herein as povidone, are produced commercially as a series of products having mean molecular weights ranging from about 10,000 to 700,000. The polymers are prepared by heating the vinyl pyrrolidone monomer in the presence of $H_2O_2$ and $NH_3$. These polymers are commercially available from a number of supplies such as Aldrich Chemical Co.

AA, MVE/MAC and DS are commercially available from a number of different suppliers. CA is available from FMC Corporation, Philadelphia, Pa.

The assay is normally performed using standard 96 well microtiter plates. If the reaction is performed in the microtiter plates, the reaction is stopped by addition of acid, the same as with the standard TMB assay. If precipitate is formed, the reaction is stopped by removal of the liquid. In contrast to other procedures using a precipitated color product of TMB, the blue precipitate does not fade over a period of several months when stored dry in the dark.

The AA, MVE/MAC, DS and CA reagents can also be used in DNA blotting and protein blotting, and possibly histochemistry, since a precipitate is formed.

Optimal concentrations of the different reagents may depend in part upon the size and chemical nature of the reaction tube or membrane surface. For example, the differences in surface charge between nitrocellulose membrane and a plastic such as polycarbonate, may effect the amount of precipitate obtained by addition of AA, MVE/MAC, DS or CA.

EXAMPLE 1

Comparisons of Povidone with other synthetic polymers.

A series of polymers was added to citrate acetate buffers in polypropylene tubes. Either COnCentrations of 10% for PVP or 1% and 10% for the other polymers were prepared and mixed or vortexed periodically for approximately three to four hours. To 1.0 ml of these solutions were then added 25 $\mu$l TMB (Aldrich, m.w. 240), 120 mg dissolved in 5 mls of DMSO to yield a 100 mmolar solution.

TABLE 2

Comparison of Polymers enhancing TMB Solubility.

| Compound | Concentration (w/v), % | Appearance of solution | Effect of TMB |
|---|---|---|---|
| povidone, 10,000 mw | 10 | soluble | soluble |
| povidone, 24,000 mw | 10 | soluble | soluble |
| povidone, 40,000 mw | 10 | soluble | soluble |
| povidone, 360,000 mw | 10 | soluble but viscous | soluble |
| poly(vinyl alcohol) 88,000 mw | 1 | slightly soluble | TMB ppt |
| poly(vinyl alcohol) 88,000 mw | 10 | slightly soluble | TMB ppt |
| poly(vinyl methyl ketone) | 1 | slightly soluble | TMB ppt |
| poly(vinyl methyl ketone) | 10 | slightly soluble | TMB ppt |
| poly(vinyl methyl ether) | 1 | soluble | TMB ppt |

TABLE 2-continued

Comparison of Polymers enhancing TMB Solubility.

| Compound | Concentration (w/v), % | Appearance of solution | Effect of TMB |
| --- | --- | --- | --- |
| poly(vinyl methyl ether) | 10 | soluble | TMB ppt |
| poly(vinyl ethyl ether) (low mw) | 1 | soluble | TMB ppt |
| poly(vinyl ethyl ether) (low mw) | 10 | slightly soluble | TMB ppt |
| poly(vinyl propionate) | 1 | toluene-based product | TMB ppt |
| poly(vinyl propionate) | 10 | toluene-based product | TMB ppt |
| poly(4-vinylpyridine-co-styrene) | 1 | not very soluble | TMB ppt |
| poly(4-vinylpyridine-co-styrene) | 10 | not very soluble | TMB ppt |
| buffer only | 0 | — | TMB ppt |

The results demonstrate that of this class of polymers, only povidone increases the solubility of the TMB in aqueous buffer.

Modifications and variations of the method and compositions of the present invention, solutions for increasing the sensitivity and otherwise improving HRP-based ELISAs, will be obvious to those skilled in the art from the foregoing detailed description of the invention. Such modifications and variations are intended to come within the scope of the appended claims.

I claim:

1. A reagent for forming a colored precipitate in an array using a chromogen producing a colored product in the presence of oxidizing agents comprising
   an aqueous buffer containing a chromogen producing a colored product in the presence of oxidizing agents, substrate for perioxidase, and a peroxidase-conjugated molecule, including a polymeric compound selected from the group consisting of alginic acid, methyl vinyl ether-maleic anhydride copolymer, dextran sulfate, carrageenan and combinations thereof, wherein the colored product forms a stable precipitate with the polymeric compound.

2. The reagent of claim 1 wherein the compound is alginic acid in a concentration of between 0.1 and 1.0 mg/ml.

3. The reagent of claim 1 wherein the compound is methyl vinyl ether/maleic anhydride copolymer in a concentration of between 0.1 and 2.0 mg/ml.

4. The reagent of claim 1 wherein the compound is dextran sulfate in a concentration of between 0.1 and 2.0 mg/ml.

5. The reagent of claim 1 wherein the compound is carrageenan in a concentration of between 0.3 and 1.0 mg/ml.

6. The reagent of claim 1 further comprising monomeric or polymeric pyrrolidone.

7. The reagent of claim 6 wherein the polymeric pyrrolidone is povidone in a concentration of between 1% and 10% and the chromogen is TMB.

8. A method for forming a colored precipitate in an assay using a chromogen producing a colored product in the presence of oxidizing agents comprising
   providing an aqueous buffer containing a chromogen producing a colored product in the presence of oxidizing agents, substrate for peroxidase, and a peroxidase-conjugated molecule, including a polymeric compound selected from the group consisting of alginic acid, methyl vinyl ether-maleic anhydride copolymer, dextran sulfate, carrageenan and combinations thereof, wherein the colored product forms a stable precipitate with the polymeric compound.

9. The method of claim 8 wherein the compound is alginic acid and is added to a concentration of between 0.1 and 1.0 mg/ml.

10. The method of claim 8 wherein the compound is methyl vinyl ether/maleic anhydride copolymer and is added to a concentration of between 0.1 and 2.0 mg/ml.

11. The method of claim 8 wherein the compound is dextran sulfate and is added to a concentration of between 0.1 and 2.0 mg/ml.

12. The method of claim 8 further comprising providing monomeric or polymeric pyrrolidone in the buffer.

13. The method of claim 12 further comprising providing TMB as a chromogen, wherein the polymeric pyrrolidone is povidone in a concentration of between 1% and 10%.

14. The method of claim 8 further comprising providing a chromogen selected from the group consisting of TMB, chloro/naphthol, diaminobenzidine tetrahydrochloride, aminoethylcarbizole, and ortho phenylenediamine.

15. The method of claim 14 further comprising providing horseradish peroxidase and a substrate for horseradish peroxidase.

* * * * *